United States Patent [19]

Sun et al.

[11] Patent Number: 5,641,782
[45] Date of Patent: Jun. 24, 1997

[54] 3-AROMATIC AND 3-HETEROAROMATIC SUBSTITUTED BISNAPHTHALIMIDES

[75] Inventors: Jung-Hui Sun, Hockessin, Del.; Steven P. Seitz, Swarthmore, Pa.

[73] Assignee: The DuPont Merck Pharmaceutical Company, Wilmington, Del.

[21] Appl. No.: 389,603

[22] Filed: Feb. 16, 1995

[51] Int. Cl.$^6$ .................. A61K 31/505; C07D 239/24; C07D 403/14
[52] U.S. Cl. .................. 514/256; 514/296; 544/335; 546/99; 546/100
[58] Field of Search .................. 514/256, 296; 544/335; 546/99, 100

[56] References Cited

U.S. PATENT DOCUMENTS

| | | | |
|---|---|---|---|
| 4,841,052 | 6/1989 | Harnisch et al. | 544/361 |
| 4,874,863 | 10/1989 | Brana et al. | 540/99 |
| 5,206,249 | 4/1993 | Sun | 514/296 |
| 5,329,048 | 7/1994 | Sun | 564/448 |
| 5,376,664 | 12/1994 | Kaltenbach, III et al. | 514/296 |
| 5,416,089 | 5/1995 | Patten et al. | 514/284 |

FOREIGN PATENT DOCUMENTS

| | | |
|---|---|---|
| 0281902 | 9/1988 | European Pat. Off. |
| 9217454 | 10/1992 | WIPO . |
| 9312092 | 6/1993 | WIPO . |
| 9402466 | 2/1994 | WIPO . |

OTHER PUBLICATIONS

Horiguchi et al. Bisnaphthalimido fluorescent whiteners. 1976. p. 85.

*Primary Examiner*—Yogendra N. Gupta
*Attorney, Agent, or Firm*—Karen H. Kondrad

[57] ABSTRACT

This invention relates to 3-Pyrimidinyl Bisnaphthalimides as Anticancer Agents and pharmaceutically acceptable salts thereof, of the formula:

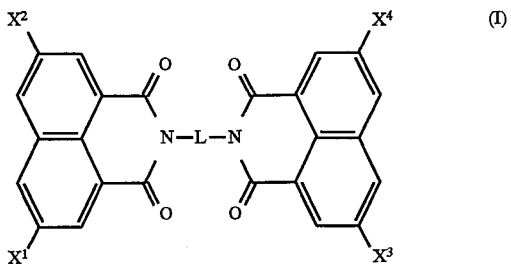

and processes for the preparation of such compounds, pharmaceutical composition containing such compounds, and methods of using such compounds to treat cancer, particularly solid tumor carcinomas, in mammals.

16 Claims, No Drawings

3-AROMATIC AND 3-HETEROAROMATIC SUBSTITUTED BISNAPHTHALIMIDES

FIELD OF THE INVENTION

This invention relates to 3-aryl and 3-heteroaryl substituted bisnaphthalimides and pharmaceutically acceptable salts thereof, of the formula:

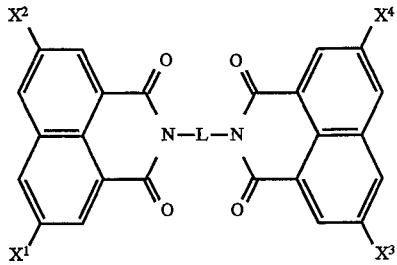

and processes for the preparation of such compounds, pharmaceutical composition containing such compounds, and methods of using such compounds to treat cancer, particularly solid tumor carcinomas, in mammals.

BACKGROUND OF THE INVENTION

Harnish et al., U.S. Pat. No. 4,841,052 describes naphthalic acid imides useful as charge-regulating substances in electrophotographic toners. Brana et al., U.S. Pat. No. 4,874,863 issued Oct. 17, 1989, discloses anticancer compounds of the formula:

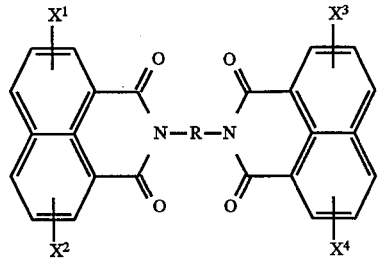

wherein $X^1$, $X^2$, $x^3$ and $X^4$ are identical or different and are each H, $NO_2$, $NH_2$, $C_1$–$C_6$-alkylamino, di-$C_1$–$C_6$-alkylamino, OH, $C_1$–$C_6$-alkoxy, halogen, trihalomethyl, $C_1$–$C_6$-alkyl, formyl, $C_1$–$C_6$-alkylcarbonyl, ureyl, $C_1$–$C_6$-alkylureyl and R is a straight chain or branched $C_4$–$C_{10}$-alkylene which is interrupted at one or two points in the chain by a secondary or tertiary amino group, where 2 nitrogen atoms may additionally be bonded to one another by an alkylene group, or a salt with a physiologically tolerated acid.

Ardecky et al., U.S. Pat. No. 5,086,059, discloses certain symmetrical bisimide compounds.

Sun, U.S. Pat. No. 5,206,249, also discloses symmetrical naphthalimide compounds.

Horiguchi et al., Chem Abstr. 1972, 76, 87174a, discloses fluorecent fused ring whitening agents of formula:

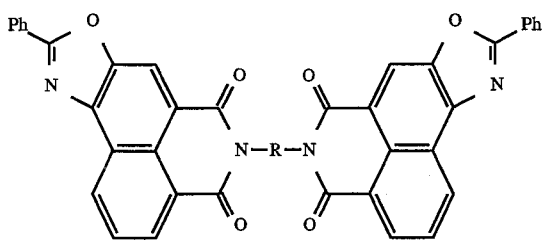

None of the above cited references describes novel bisnaphthalimide tumoricidal compounds with pendant aryl or heteroaryl groups.

DETAILED DESCRIPTION OF THE INVENTION

There is provided by this invention bisnaphthalimides compounds having the formula:

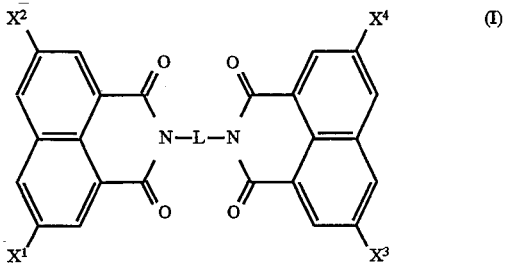

and enantiomeric or diastereomeric forms thereof, or mixtures of enantiomeric or diastereomeric forms thereof, or pharmaceutically acceptable salts thereof, wherein:

L is:

a)

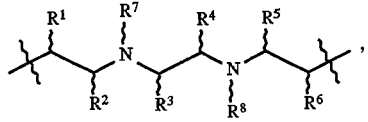

or b)

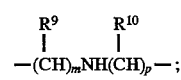

$R^1$, $R^2$, $R^3$, $R^4$, $R^5$, $R^6$, $R^9$ and $R^{10}$ are independently selected from the group: H, $CH_3$ or $C_2H_5$;

$R^7$ and $R^8$ are independently selected from the group consisting of H or $CH_3$;

$X^1$, $X^2$, $X^3$, $X^4$ are independently selected from the group consisting of: H, $NO_2$, aryl, or heteroaryl, where aryl or heteroaryl may be optionally substituted with 0–2 groups independently selected from:

$C_1$–$C_2$ alkyl, $C_1$–$C_2$ alkoxy, CN, $NO_2$, halogen, aminocarbonyl, mono($C_1$–$C_2$ alkyl)aminocarbonyl, di($C_1$–$C_2$ alkyl)aminocarbonyl, amino, $C_1$–$C_2$ alkoxycarbonyl, hydroxycarbonyl, mono($C_1$–$C_2$ alkyl)amino, di($C_1$–$C_2$ alkyl)amino, $C_1$–$C_2$ alkylsulfonyl, mono($C_1$–$C_2$ alkyl)aminosulfonyl, and di($C_1$–$C_2$ alkyl)aminosulfonyl;

aryl is a phenyl group;

heteroaryl is an optionally substituted 5- or 6-membered heteroaromatic ring independently selected at each occurrence from the group consisting of:

furanyl, furazanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, thienyl, triazinyl, and triazolyl;

m is 1, 2 or 3;

p is 1, 2, 3 or 4;

provided that:

1) at least one of $X^1$ and $X^2$ are aryl or heteroaryl.

Preferred compounds of the present invention include compounds of formula (I), and pharmaceutically acceptable salts thereof, and enantiomeric or diastereomeric forms thereof, wherein:

$R^1$, $R^2$, $R^3$, $R^4$, $R^5$, $R^6$ and $R^9$ are independently selected from the group: H or $CH_3$;

$R^7$ and $R^8$ are independently selected from the group: H or $CH_3$;

$R^{10}$ is H;

$X^1$ and $X^2$ are as follows:
1) $X^1$ is optionally substituted and is aryl or heteroaryl when $X^2$ is $NO_2$; or
2) $X^1$ is optionally substituted and is aryl or heteroaryl when $X^2$ is H;

$X^3$ and $X^4$ are as follows:
1) $X^3$ is optionally substituted and is aryl or heteroaryl when $X^4$ is $NO_2$;
2) $X^3$ is optionally substituted and is aryl or heteroaryl when $X^4$ is H; or
3) $X^3$ is H when $X^4$ is $NO_2$;

$X^1$ and $X^3$, when aryl or heteroaryl, are independently optionally substituted with 0–2 groups selected from:
$C_1$–$C_2$ alkyl, $C_1$–$C_2$ alkoxy, CN, $NO_2$, halogen, aminocarbonyl, mono($C_1$–$C_2$ alkyl)aminocarbonyl, di($C_1$–$C_2$ alkyl)aminocarbonyl, amino, $C_1$–$C_2$ alkoxycarbonyl, hydroxycarbonyl, mono($C_1$–$C_2$ alkyl)amino, di($C_1$–$C_2$ alkyl)amino;

heteroaryl is an optionally substituted 5- or 6-membered heteroaromatic ring independently selected at each occurrence from the group consisting of:
furanyl, imidazolyl, isothiazolyl, isoxazolyl, oxazolyl, pyrazinyl, pyrazolyl, pyridazinyl, pyridyl, pyrimidinyl, pyrrolyl, thiazolyl, thienyl, and triazinyl;

m is 2 or 3;

p is 3 or 4.

More preferred compounds of the present invention include compounds of formula (I), and pharmaceutically acceptable salts thereof, and enantiomeric or diastereomeric forms thereof, wherein:

L is

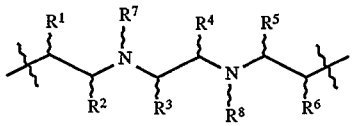

$R^1$, $R^6$ are $CH_3$;

$R^2$, $R^3$, $R^4$, $R^5$, $R^7$, and $R^8$ are H;

$X^1$ is optionally substituted heteroaryl;

$X^2$ is H;

$X^3$ and $X^4$ are as follows:
1) $X^3$ is optionally substituted heteroaryl when $X^4$ is H; or
2) $X^3$ is H when $X^4$ is $NO_2$;

$X^1$ and $X^3$, when heteroaryl, are independently optionally substituted with 0–2 groups selected from:
$CH_3$, $NO_2$, hydroxycarbonyl, mono($C_1$–$C_2$ alkyl) amino, or di($C_1$–$C_2$ alkyl)amino;

heteroaryl is an optionally substituted 5- or 6-membered heteroaromatic ring independently selected at each occurrence from the group consisting of:
furanyl, isothiazolyl, isoxazolyl, pyrazolyl, pyridyl, pyrazinyl, pyrimidinyl, pyridazinyl, and pyrrolyl.

Most preferred compounds of the present invention include compounds of formula (I), and pharmaceutically acceptable salts thereof, and enantiomeric or diastereomeric forms thereof, wherein:

$X^1$ and $X^3$, when heteroaryl, are independently substituted with 0–1 $CH_3$;

heteroaryl is an optionally substituted 5- or 6-membered heteroaromatic ring independently selected at each occurrence from the group consisting of: isoxazolyl, pyridyl, and pyrimidinyl.

The specifically preferred compounds of the present invention include:

[R-(R*,R*)]-2,2'-[1,2-ethanediylbis[imino(1-methyl-2,1-ethanediyl)]]bis[5-(5-pyrimidinyl)-1H-benz(de)isoquinoline-1,3(2H)-dione]methanesulfonate (1:2),

[R-(R*,R*)]-2-[1-methyl-2-[[2-[[2-[5-(3-methyl-5-isoxazolyl)-1,3-dioxo-1H-benz(de)isoquinolin-2(3H)-yl]propyl]amino]ethyl]amino]ethyl]-5-nitro-1H-benz(de)isoquinoline-1,3(2H)-dione methanesulfonate (1:2),

[R-(R*,R*)]-2-[1-methyl-2-[[2- [[2-(5-nitro-1,3-dioxo-1H-benz(de)isoquinolin-2(3H)-yl) propyl]amino]ethyl]amino]ethyl]-5 -(2 -pyridinyl )-1H-benz(de)isoquinoline-1,3(2H)-dione methanesulfonate (1:2),

[R-(R*,R* )]-2-[1-methyl-2-[[2-[[2-(5-nitro-1,3-dioxo-1H-benz(de)isoquinolin-2(3H)-yl)propyl]amino]ethyl]amino]ethyl]-5-(5-pyrimidinyl )-1H-benz(de)-isoquinoline-1,3(2H)-dione methanesulfonate (1:2),

[R-(R*,R*)]-2-[1-methyl-2-[[2-[[2-(5-nitro-1,3-dioxo-1H-benz(de)isoquinolin-2(3H)-yl)propyl]amino]ethyl]amino]ethyl]-5-(2-pyrimidinyl)-1H-benz(de)-isoquinoline-1,3(2H)-dione methanesulfonate (1:2),

[S-(R*,R*)]-2,2'-[1,2-ethanediylbis[imino(1-methyl-2,1-ethanediyl)]]bis[5-(5-pyrimidinyl)-1H)-benz(de)isoquinoline-1,3(2H)-dione]methanesulfonate (1:2),

[S-(R*,R*)]-2-[1-methyl-2-[[2-[[2-[5-(3-methyl-5-isoxazolyl)-1,3-dioxo-1H-benz(de)isoquinolin-2 (3H)-yl]propyl]amino]ethyl]amino]ethyl]-5-nitro-1H-benz(de)isoquinoline-1,3(2H)-dione methanesulfonate (1:2),

[S-(R*,R*)]-2-[1-methyl-2-[[2-[[2-(5-nitro-1,3-dioxo-1H-benz(de)isoquinolin-2(3H)-yl)propyl]amino]ethyl]amino]ethyl]-5-(2-pyridinyl)-1H-benz(de)isoquinoline-1,3 (2H)-dione methanesulfonate (1:2),

[S-(R*,R*)]-2-[1-methyl-2-[[2-[[2-(5-nitro-1,3-dioxo-1H-benz(de)isoquinolin-2(3H)-yl)propyl]amino]ethyl]amino]ethyl]-5-(5-pyrimidinyl)-1H-benz(de)-isoquinoline-1,3(2H)-dione methanesulfonate (1:2),

[S-(R*,R*)]-2-[1-methyl-2-[[2-[[2-(5-nitro-1,3 -dioxo-1H-benz(de)isoquinolin-2(3H)-yl)propyl]amino]ethyl]amino]ethyl]-5-(2-pyrimidinyl )-1H-benz(de)-isoquinoline-1,3(2H)-dione methanesulfonate (1:2), (R*,S*)-2,2'-[1,2-ethanediylbis[imino(1-methyl-2,1-ethanediyl)]]bis[5-(5-pyrimidinyl)-1H-benz(de)isoquinoline-1,3(2H)-dione]methanesulfonate (1:2), (R*,S*)-2-[1-methyl-2-[[2-[[2-[5-(3-methyl-5-isoxazolyl )-1,3 -dioxo-1H-benz(de)isoquinolin-2(3H)-yl ]propyl ]amino]ethyl ]amino]ethyl ]-5-nitro-1H-benz(de)
isoquinoline-1,3(2H)-dione methanesulfonate (1:2), (R*,S*)-2-[1-methyl-2-[[2-[[2-(5-nitro-1,3-dioxo-1H-benz(de)isoquinolin-2(3H)-yl)propyl]amino]ethyl]
amino]ethyl]-5-(2-pyridinyl)-1H-benz(de)
isoquinoline-1,3(2H)-dione methanesulfonate (1:2), (R*,S*)-2-[1-methyl-2-[[2-[[2-(5-nitro-1,3-dioxo-1H-benz(de)isoquinolin-2(3H)-yl )propyl]amino]ethyl]
amino]ethyl ]-5-(5-pyrimidinyl )-1H-benz(de)-isoquinoline-1,3(2H)-dione methanesulfonate (1:2), (R*,S* )-2-[1-methyl-2-[[2-[[2-(5-nitro-1,3 -dioxo-1H-benz(de)isoquinolin-2(3H)-yl)propyl]amino]ethyl]
amino]ethyl]-5-(2-pyrimidinyl)-1H-benz(de)-isoquinoline-1,3(2H)-dione methanesulfonate (1:2);

and pharmaceutically acceptable salts thereof.

It should be recognized that the above-identified groups of compounds are preferred embodiments of this invention, but that their description herein is in no way intended to limit the overall scope of this invention.

Also provided by this invention are processes for the preparation of the above described compounds of formula (I), pharmaceutical compositions comprising the acceptable carrier, and methods of using these compounds for the treatment of cancer, particularly solid tumor carcinomas, in a mammal.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the room temperature to the solvent's boiling temperature. A given reaction may be carried out in one solvent or a mixture of more than one solvent. Depending on the particular reaction step, suitable solvents for a particular reaction step may be selected.

Suitable halogenated solvents include: chloroform, dichloromethane, tetrachloroethylene, or 1,1-dichloroethane.

Suitable ether solvents include: tetrahydrofuran, or 1,4-dioxane.

Suitable protic solvents may include, by way of example and without limitation, methanol, ethanol, ethylene glycol, 1-propanol, or 2-propanol.

Suitable aprotic solvents may include, by way of example and without limitation, dimethylformamide (DMF), dimethylacetamide (DMAC), acetonitrile, dimethyl sulfoxide (DMSO), or ethyl acetate.

The compounds herein described may have asymmetric centers. All chiral, enantiomeric, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, enantiomeric, diastereomeric, racemic forms and all geometric isomeric forms of a structure are intended, unless the specific stereochemistry or isomer form is specifically indicated.

When any variable (for example, $R^1$, $R^2$, $R^3$, $R^4$, m, etc.) occurs more than one time in any constituent or formula for a compound, its definition on each occurrence is independent of its definition at every other occurrence. Thus, for example, if a group is shown to be substituted with 0–3 $R^1$, then said group may optionally be substituted with up to three $R^1$ and $R^1$ at each occurrence is selected independently from the defined list of possible $R^1$. Also, combinations of substituents and/or variables are permissible only if such combinations result in stable compounds. By stable compound or stable structure it is meant herein a compound that is sufficiently robust to survive isolation to a useful degree of purity from a reaction mixture.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge.

The terms "-(alkyl)-", "-(alkyenyl)-", "-(phenyl)-", and the like, refer to alkyl, alkenyl, and phenyl groups, respectively, which are connected by two bonds to the rest of the structure of Formula (I). Such groups may alternatively and equivalently be denoted as "alkylene", "alkenylene", "phenylene", and the like, respectively.

"Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl.

As used herein, the term "heteroaryl" is intended to mean a stable aromatic 5- or 6-membered heterocyclic ring which contains heteroatoms selected from N, S and/or O. The heteroaryl ring may be attached to its pendant group at any nitrogen or carbon atom which results in a stable structure. The heteroaryl rings described herein may be substituted on carbon or on a nitrogen atom if the resulting compound is stable. Examples of such heteroaryls include, but are not limited to, furanyl, furazanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, thienyl, triazinyl, and triazolyl.

When a bond to a substituent is shown to cross the bond connecting two atoms in a ring, then such a substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like dichloromethane, ethyl acetate, ethanol, methanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

SYNTHESIS

The compounds of the present invention may be prepared according to the following schemes and examples, using appropriate materials and are further exemplified by the specific examples which follow. Those skilled in the art will readily understand that known variations of the conditions and processes of the following preparative procedures can be used to prepare those compounds. Compounds of the present invention can also be prepared using methods known in the art of organic synthesis. The references cited below are all incorporated herein by reference.

Symmetrical compounds (3) of formula (I) can be prepared by condensing a naphthalic anhydride (1) with a polyamine (2) in a suitable solvent, such as methanol (MeOH), ethanol (EtOH), propanol (PrOH), isopropanol (i-PrOH), tetrahydrofuran (THF), dioxane, dioxolane, dimethylacetamide (DMAC), dimethylsulfoxide (DMSO), acetonitrile (ACN) or dimethylformamide (DMF), at temperatures ranging from ambient to the solvent's boiling point. The free base of the bisimide derivative may be isolated from the reaction mixture or the mixture may be acidified with an appropriate mineral or organic acid to produce a pharmaceutically acceptable salt. The materials are generally obtained by filtration of the reaction mixture. The salt can also be prepared by acidifying a suspension or solution of the isolated free base in ethanol or dichloromethane with the appropriate acid and collecting the thus formed solid by filtration. In some cases, the free base requires purification by column chromatography before its salt can be prepared.

The polyamines are either commercially available or prepared as described in U.S. Pat. No. 5,206,249.

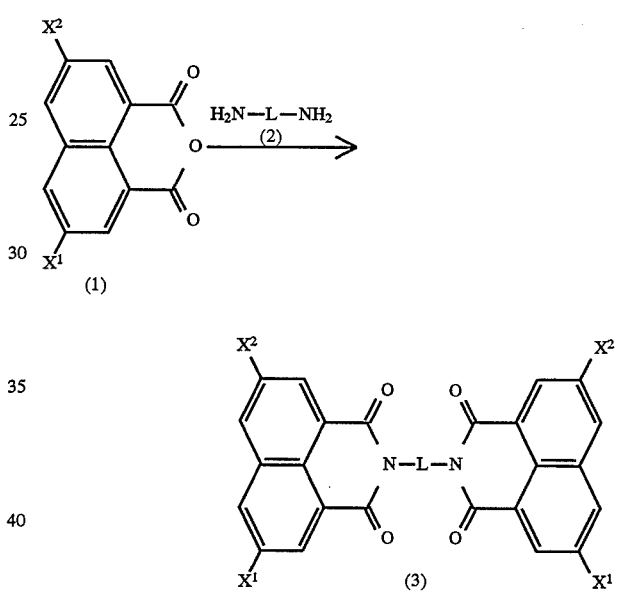

Scheme 1.
Synthesis of symmetrical compounds (3)
of formula (I)

The unsymmetrical compounds (5) of formula (I) can be prepared by reacting a polyamine (2) with equimolar amounts of two different anhydrides (1) and (4) and separating the statistical mixture of products by column chromatography as shown in Scheme 2.

Scheme 2.
Synthesis of unsymmetrical compounds (5)
of formula (I)

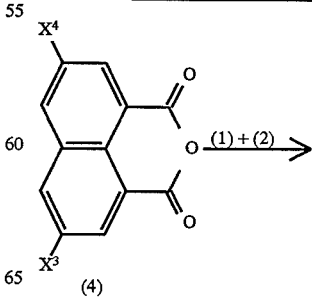

Scheme 2.
Synthesis of unsymmetrical compounds (5) of formula (I)

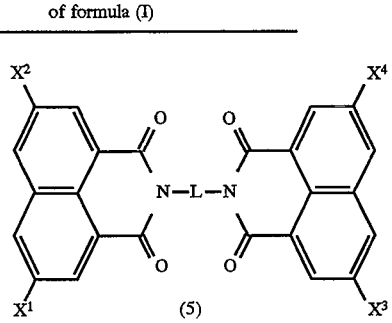

Unsymmetrical compounds (5) of formula (I) can also be prepared by reacting a suitable monoimide, prepared as described in U.S. patent application Ser. No. 07/919,227, with one equivalent of an anhydride. For example, Scheme 3 shows the synthesis of an unsymmetrical compound (5) from reaction of naphthalic anhydride (4) with monoimide (6).

Scheme 3.
Synthesis of unsymmetrical compounds of formula (I)

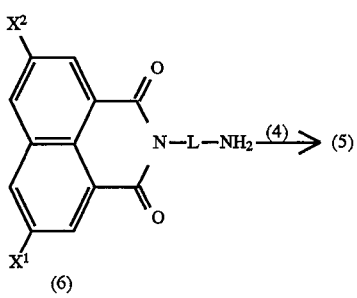

The aromatic or heteroaromatic substituted naphthalic anhydrides (1) or (4) utilized for the preparation of the compounds provided by this invention are novel. They are prepared by Methods A-C as shown in Schemes 4 and 5, and are summarized in Table 1. 3-Bromo-1,8-naphthalic anhydride (7) was coupled with an aryltrialkyltin (8) in the presence of bis(triphenylphosphine)palladium (II) chloride as a catalyst in dioxane at refluxing temperature to give (1) or (4) (Method A, Scheme 4). Alternatively, (7) was reacted with hexamethylditin and tetrakis(triphenylphosphine) palladium (0) in toluene at reflux which furnished 3-(trimethylstannyl)-1,8-naphthalic anhydride (9). Compound 9, in turn, was coupled with an aryl halide (10) to yield (1) or (4) (Method B, Scheme 4).

Scheme 4.
Synthesis of aryl substituted naphthalic anhydrides (1) or (4)

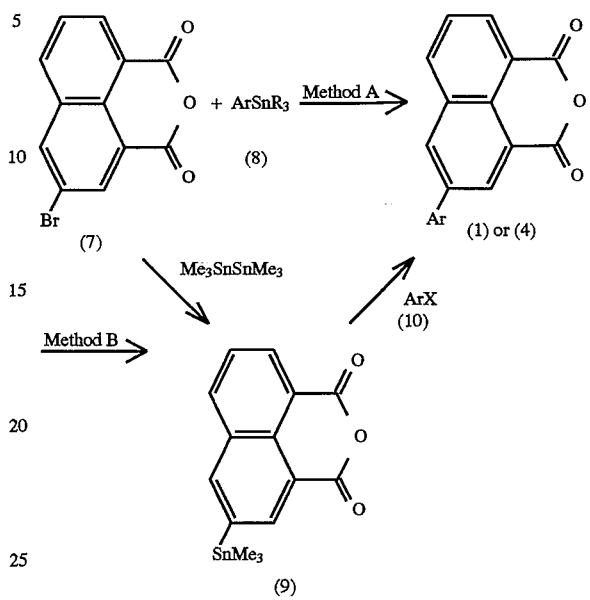

Scheme 5 depicts the synthesis of 3-(1-pyrrolyl)-1,8-naphthalic anhydride (11) by reaction of 3-amino-1,8-naphthalic anhydride with 2,5-dimethoxytetrahydrofuran in acetic acid at reflux.

Scheme 5.
Synthesis of 3-(pyrrolyl)-1,8-naphthalic anhydride (11)

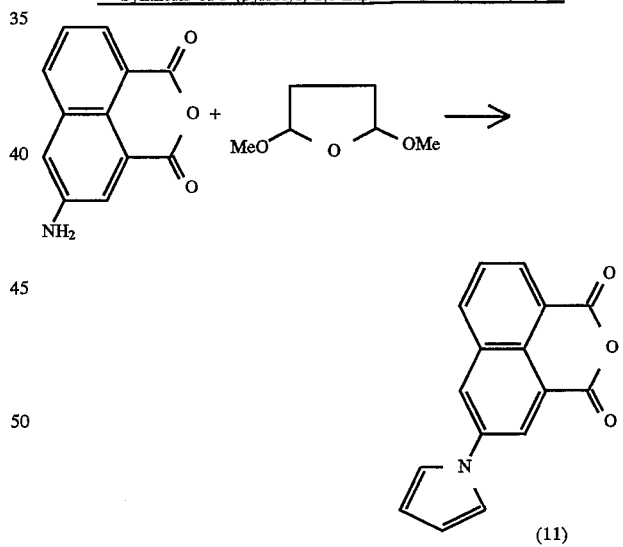

EXAMPLES

The invention can be further understood by referring to the following examples. However, the following examples and preparations are for illustrative purposes only and are not to be construed as limiting the invention.

Abbreviations used in the Examples are defined as follows: "°C." for degrees Celsius, "nmr" or "NMR" for nuclear magnetic resonance spectroscopy, "br s" for broad singlet, "s" for singlet, "d" for doublet, "dd" for doublet of doublets, "m" for multiplet, "t" for triplet, "eq" for equivalent or equivalents, "g" for gram or grams, "mg" for milligram or milligrams, "mL" for milliliter or milliliters, "mmol" for millimole or millimoles, "H" for hydrogen or hydrogens, "$^1$H" for proton, "h" for hour or hours, "M" for molecular weight, "min" for minute or minutes, "mp" for melting point range, "MHz" for megahertz, "MS" for mass spectroscopy, "IR" for infrared spectroscopy, "tlc" for thin layer chromatography, Preparation of 3-aromatic or 3-heteroaromatic substituted 1,8-naohthalic anhydrides Method A: 3-[5-(3-methylisoxazolyl)]-1,8-naphthalic anhydride: A mixture of 3-bromo-1,8-naphthalic anhydride (1.35 g, 4.87 mmol), 3-methyl-5-(tributylstannyl)isoxazole (Y. Kondo, et al., *Tetrahedron Lett.*, 1989, 30, 4249) (2.82 g, 7.58 mmol) and bis(triphenylphosphine)palladium (II) chloride (0.35 g, 0.5 mmol) in 70 mL of dioxane was heated to reflux for 21 h. After the mixture was cooled to room temperature, the solvent in the mixture was evaporated to dryness. The residue was added 100 mL of dichloromethane, and the yellow solid was collected on a filter, washed with dichloromethane (25 mL) to give 0.77 g (58% yield) of product: mp 306°–307° C. $^1$H NMR (TFA-d$_1$) δ9.26 (s, 1H), 9.09 (s, 1H), 8.99 (s, 1H), 8.71 (d, 1H), 8.14 (t, 1H), 7.15 (s, 1H), 2.69 (s, 3H).

Method B: 3-(5-pyrimidinyl)-1,8-naphthalic anhydride:

Part 1: 3-(trimethylstannyl)-1,8-naphthalic anhydride: A mixture of 3-bromo-1,8-naphthalic anhydride (3.5 g, 12.6 mmol), hexamethylditin (5.0 g, 15.3 mmol) and tetrakis (triphenylphosphine)palladium (0) (0.47 g, 0.41 mmol) in 50 mL of toluene was heated to reflux for 16 h. After being cooled to room temperature, the reaction mixture was diluted with 150 mL of Et$_2$O. The solid was collected on a filter to produce 2.89 g (64% yield) of product: mp 173°–173.9° C. $^1$H NMR (CDCl$_3$) δ8.73 (s, 1H), 8.60 (d, 1H, J=7.3 Hz), 8.40 (s, 1H), 8.30 (d, 1H, J=8.0 Hz), 7.80 (t, 1H, J=8.0 Hz), 0.45 (s, 9H). MS 380 (M+NH$_4$).

Part 2: 3-(5-pyrimidinyl)-1,8-naphthalic anhydride: A mixture of 3-trimethylstannyl-1,8-naphthalic anhydride (9.01 g, 24.96 mmol), 5-bromopyrimidine (4.37 g, 27.49 mmol) and bis(triphenylphosphine)palladium (II) chloride (0.88 g, 1.25 mmol) in 200 mL of dioxane was heated to reflux for 20 h. After the reaction mixture was cooled to room temperature, the solid was collected on a filter to furnish 5.62 g (82% yield) of product as a grey solid: mp 282°–283° C. $^1$H NMR (TFA-d$_1$) δ10.04 (s, 2H), 9.93 (s, 1H), 9.23 (s, 1H), 9.05 (s, 1H), 9.00 (d, 1H), 8.73 (d, 1H), 8.16 (t, 1H). MS 294 (M+NH$_4$) and 277 (M+H).

Method C: 3-(1-pyrrolyl)-1,8-naphthalic anhydride: A mixture of 3-amino-1,8-naphthalic anhydride (R. W. Middleton & J. Parrick, *J. Heterocyclic Chem.*, 1986, 23, 849) (2.0 g, 9.38 mmol) and 2,5-dimethoxytetrahydrofuran (1.24 g, 9.38 mmol) in 6 mL of acetic acid was heated to reflux for 30 min. The solvent in the reaction solution was evaporated and the remaining residue was flash chromatographed (100% dichloromethane) to give 1.02 g (41% yield) of product as a yellow solid; mp 224°–225° C. $^1$H NMR (CDCl$_3$) δ8.70 (d, 1H), 8.59 (d, 1H), 8.32 (d, 1H), 8.23 (d, 1H), 7.86 (t, 1H), 7.30 (dd, 2H), 6.48 (d, 2H). MS 281 (M+NH$_4$) and 264 (M+H).

EXAMPLE 47

[R-(R*,R*)]-2,2'-[1,2-ethanediylbis[imino(1-methyl-2,1-ethanediyl)]]bis[5-(5-pyrimidinyl)-1H-benz (de) isoquinoline-1,3(2H)-dione]methanesulfonate (1:2)

A mixture of 3-(5-pyrimidinyl)-1,8-naphthalic anhydride (0.55 g, 2.0 mmol) and (R,R)-N$^1$,N$^{1'}$-1,2-ethanediylbis (1,2-propanediamine) (Sun, U.S. Pat. No. 5,206,249) (0.176 g, 1.0 mmol) in 10 mL of THF was heated to reflux for 24 h. The solvent in the reaction mixture was evaporated. The remaining residue was flash chromatographed (NH$_4$OH/ CH$_3$OH/CH$_2$Cl$_2$, from 0:0:100 to 0.2:10:100) to give 0.29 g (42% yield) of the free base. A solution of the free base (0.26 g, 0.38 mmol) in 5 mL of dichloromethane was added a solution of methanesulfonic acid (75 mg, 0.78 mmol) in dichloromethane. After the mixture was stirred at room temperature for 6 h, the solid was collected on a filter, washed with dichloromethane and diethyl ether to furnish crude product (0.32 g, 40% yield). This was suspended in 10 mL of methanol and heated to reflux for 1 h. The solid was isolated by filtration to yield 0.26 g (33% yield) of pure product: mp 234°–236° C. $^1$H NMR (DMSO-d$_6$) δ9.38 (s, 4H), 9.32 (s, 2H), 9.00 (d, 2H), 8.84 (d, 2H), 8.75 (br, 4H), 8.56 (s, 2H), 8.54 (s, 2H), 7.98 (t, 2H), 5.49 (br, 2H), 3.88 (br, 2H), 3.50–3.20 (m, 6H), 2.25 (s, 6H), 1.58 (d, 6H). MS 691 (M+H). IR (KBr) 3444, 1704, 1662 cm$^{-1}$. Anal. Calcd for C$_{40}$H$_{34}$N$_8$O$_4$·2CH$_3$SO$_3$H: C, 57.00; H, 4.60; N, 12.45; S. 7.30. Found: C, 57.13; H, 4.79; N, 12.69; S, 7.26.

EXAMPLE 145

2-[3-[[2-[1,3-dioxo-5-(5-pyrimidinyl)-1H-benz(de) isoquinolin-2(3H)-yl]-ethyl]amino]propyl]-5-(5-pyrimidinyl)-1H-benz(de)isoquinoline-1,3(2H)-dione methanesulfonate (1:1)

A mixture of 3-(5-pyrimidinyl)-1,8-naphthalic anhydride (0.50 g, 1.81 mmol) and N-(2-aminoethyl)-1,3-propanediamine (0.12 g, 1.02 mmol) in 40 mL of ethanol was heated to reflux for 21 h. The solid was collected on a filter while hot, washed with ethanol, dried to give 0.36 g (60% yield) of the free base as a grey solid. The free base was added 40 mL of methanol and 0.03 mL (0.46 mmol) of methanesulfonic acid. The mixture was heated to reflux for 19 h. The grey solid was collected on a filter to provide 0.21 g of crude product. The crude product was suspended in 20 mL of methanol and then heated to reflux for 10 min. After the mixture was cooled to room temperature, the solid was collected on a filter to give 0.10 g (17% yield) of pure product: mp 254°–255° C. $^1$H NMR (TFA-d$_1$) δ10.00 (d, 2H), 9.90 (s, 1H), 9.2 (m, 2H), 9.0–8.8 (m, 3H), 8.73–8.5 (m, 4H), 8.1–7.9 (m, 2H), 7.75 (br s, 2H), 4.93 (br s, 2H), 4.55 (br s, 2H), 3.90 (br s, 2H), 3.59 (br s, 2H), 3.05 (s, 3H), 2.50 (br s, 2H). MS 634 (M+H).

EXAMPLE 150

[R-(R,R*)]-2-[1-methyl-2-[[2-[[2-[5-(3-methyl-5-isoxazolyl)-1,3-dioxo-1H-benz(de)isoquinolin-2(3H) -yl]propyl]amino]ethyl]amino]ethyl]-5-nitro- 1H-benz(de)isoquinoline-1,3(2H)-dione methanesulfonate (1:2)

A mixture of [R-(R*,R*)]-2-[2-[[2-[(2-aminopropyl) amino]ethyl]amino]-1 -methyl ethyl]-5 -nitro-1H-benz [de] isoquinoline-1,3(2H)-dione (1.45 g, 3.56 mmol) and 3-[5-(3-methyl)isoxazolyl]-1,8-naphthalic anhydride (1.00 g, 3.63 mmol) in 30 mL of DMF was heated at 60° C. for 22 h. The solvent in the reaction solution was evaporated to give 2.48 g of a red residue. This free base was added 100 mL of methanol and 0.49 mL (7.55 mmol) of methanesulfonic acid. After the mixture was heated at reflux for 21 h, the solid was collected on a filter while hot to furnish 0.62 g (19% yield): mp 204°–206° C.; crop 2, 0.38 g (12% yield). $^1$H NMR (TFA-d$_1$) δ9.42 (s, 1H), 9.38 (s, 1H), 9.10 (s, 1H), 8.98 (s, 1H), 8.90 (d, 1H), 8.80 (d, 1H), 8.65 (d, 1H), 8.59 (d, 1H), 8.09 (dr, 2H), 7.20 (s, 1H), 5.90 (m, 2H), 4.42 (m, 2H), 4.00 (m, 4H), 3.78 (d, 2H), 2.80 (s, 6H), 2.70 (s, 3H), 1.80 (s, 6H). MS 661 (M+H).

Tables 1–8 show compounds of this invention which may be prepared using methods disclosed herein.

TABLE 1

Novel 3-aryl and 3-heteroaryl-1,8-naphthalic anhydrides

| No | X$^1$ | X$^2$ | Method | Yield (%) | mp (°C.) |
|---|---|---|---|---|---|
| 1 | phenyl | H | A | 48 | 212–214 |
| 2 | 4-OMe-phenyl | H | A | 33 | 189–191 |
| 3 | 3-methylisoxazol-5-yl | H | A | 58 | 306–307 |
| 4 | 3-methylisoxazol-5-yl | NO$_2$ | A | 53 | 323–325 |
| 5 | 3-CO$_2$Et-isoxazol-5-yl | H | A | NA | NA |
| 6 | 4-NO$_2$-phenyl | H | B | 65 | NA |
| 7 | thienyl | H | B | 32 | 204–205 |
| 8 | pyridyl | H | B | 38 | 234–235 |
| 9 | 3-NO$_2$-pyridyl | H | B | 72 | 298–300 (d) |
| 11 | pyrimidinyl | H | B | 82 | 282–283 |
| 12 | pyridyl | H | B | 76 | 334–335 |
| 13 | pyrrolyl (N-linked) | H | C | 41 | 224–225 |
| 14 | pyridyl | H | B | | |
| 15 | pyridyl | H | B | | |
| 16 | pyrimidinyl | H | B | | |
| 17 | pyrimidinyl | H | B | | |
| 18 | pyridazinyl | H | B | | |
| 19 | pyridazinyl | H | B | | |
| 20 | pyrrolyl (NH) | H | B | | |

TABLE 1-continued

Novel 3-aryl and 3-heteroaryl-1,8-naphthalic anhydrides

| No | X¹ | X² | Method | Yield (%) | mp (°C.) |
|---|---|---|---|---|---|
| 21 | N-methylpyrrol-2-yl | H | B | | |
| 22 | 1H-pyrrol-3-yl | H | B | | |
| 23 | N-methylpyrrol-3-yl | H | B | | |
| 24 | thien-3-yl | H | B | | |
| 25 | fur-2-yl | H | B | | |
| 26 | fur-3-yl | H | B | | |
| 27 | isoxazol-5-yl | H | B | | |
| 28 | isoxazol-4-yl | H | B | | |
| 29 | isoxazol-3-yl | H | B | | |

TABLE 2

Symmetrical 3-aryl and 3-heteroaryl substituted bisnaphthalimides of Formula (I): L is diamino linker.

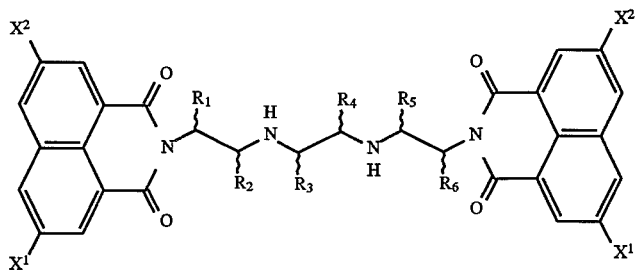

| Ex. | X¹ | X² | R¹,R²,R³,R⁴,R⁵,R⁶ | Salt | mp °C. |
|---|---|---|---|---|---|
| 30 | phenyl | H | H,H,H,H,H,H | 2 $CH_3SO_3H$ | 198–200 |

TABLE 2-continued

Symmetrical 3-aryl and 3-heteroaryl substituted bisnaphthalimides of Formula (I): L is diamino linker.

| Ex. | X$^1$ | X$^2$ | R$^1$,R$^2$,R$^3$,R$^4$,R$^5$,R$^6$ | Salt | mp °C. |
|---|---|---|---|---|---|
| 31 | 4-OMe-phenyl | H | H,H,H,H,H,H | free base | 162–164 |
| 32 | N-pyrrolyl | H | H,H,H,H,H,H | 2 CH$_3$SO$_3$H | 236–238 |
| 33 | 2-thienyl | H | H,H,H,H,H,H | free base | 215–216 |
| 34 | 3,5-dimethylisoxazolyl | H | H,H,H,H,H,H | 2 CH$_3$SO$_3$H | 255–257 |
| 35 | 3,5-dimethylisoxazolyl | H | Me(R),H,H,H,H,Me(R) | 2 CH$_3$SO$_3$H | 244–246 |
| 36 | 3,5-dimethylisoxazolyl | H | H,Me(S),H,H,Me(S),H | 2 CH$_3$SO$_3$H | 250–253 |
| 37 | 3,5-dimethylisoxazolyl | H | Et(R),H,H,H,H,Et(R) | 2 CH$_3$SO$_3$H | 244–245 |
| 38 | 3,5-dimethylisoxazolyl | H | Me(R),H,Me(S),H,Me(R),H | 2 CH$_3$SO$_3$H | NA |
| 39 | 3,5-dimethylisoxazolyl | NO$_2$ | Me(R),H,Me(S),H,Me(R),H | 2 CH$_3$SO$_3$H | 180–187 |
| 40 | 3,5-dimethylisoxazolyl | NO$_2$ | H,H,H,H,H,H | 2 CH$_3$SO$_3$H | 292–294 |

TABLE 2-continued
Symmetrical 3-aryl and 3-heteroaryl substituted bisnaphthalimides of Formula (I): L is diamino linker.
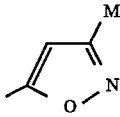
| Ex. | X¹ | X² | $R^1,R^2,R^3,R^4,R^5,R^6$ | Salt | mp °C. |
|---|---|---|---|---|---|
| 41 | 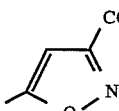 | $NO_2$ | Me(R),H,H,H,H,Me(R) | 2 $CH_3SO_3H$ | 244–246 |
| 42 | 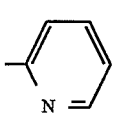 | $CO_2Et$ | H,H,H,H,H,H | free base | 205 (d) |
| 43 | 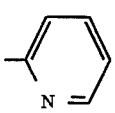 | H | H,H,H,H,H,H | 2 $CH_3SO_3H$ | 162–167 |
| 44 | 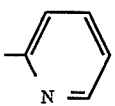 | H | Me(R),H,H,H,H,Me(R) | 2 $CH_3SO_3H$ | 218–220 |
| 45 | 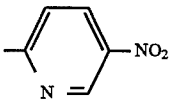 | H | Et(R),H,H,H,H,Et(R) | 2 $CH_3SO_3H$ | 222–223 |
| 46 | 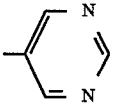 | H | H,H,H,H,H,H | free base | 227–230 |
| 47 | 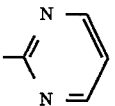 | H | Me(R),H,H,H,H,Me(R) | 2 $CH_3SO_3H$ | 234–236 |
| 48 | 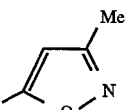 | H | Me(R),H,H,H,H,Me(R) | 2 $CH_3SO_3H$ | 200–202.5 |
| 49 | 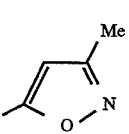 | H | H,Me(R),H,H,Me(R),H | | |
| 50 | 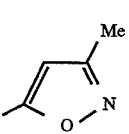 | H | H,Et(S),H,H,Et(S),H | | |

TABLE 2-continued

Symmetrical 3-aryl and 3-heteroaryl substituted bisnaphthalimides of Formula (I): L is diamino linker.

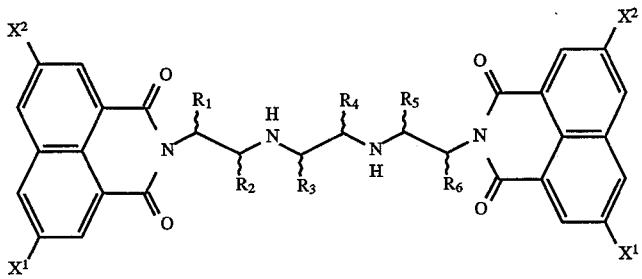

| Ex. | $X^1$ | $X^2$ | $R^1,R^2,R^3,R^4,R^5,R^6$ | Salt | mp °C. |
|---|---|---|---|---|---|
| 51 | Me / \\ / N O (isoxazole) | H | H,Et(R),H,H,Et(R),H | | |
| 52 | -pyrimidin-5-yl | H | Me(S),H,H,H,H,Me(S) | | |
| 53 | -pyrimidin-5-yl | H | Me(R),H,H,H,H,Me(S) | | |
| 54 | -pyrimidin-5-yl | H | Me(±),H,H,H,H,Me(±) | | |
| 55 | -pyrimidin-5-yl | H | H,H,H,H,H,H | | |
| 56 | -pyrimidin-5-yl | H | Me(R),H,H,H,H,H | | |
| 57 | -pyrimidin-5-yl | H | Me(S),H,H,H,H,H | | |
| 58 | -pyrimidin-5-yl | H | Me(±),H,H,H,H,H | | |
| 59 | -pyrimidin-5-yl | H | H,Me(R),H,H,Me(R),H | | |
| 60 | -pyrimidin-5-yl | H | H,Me(S),H,H,Me(S),H | | |
| 61 | -pyrimidin-5-yl | H | H,Me(±),H,H,Me(±),H | | |
| 62 | -pyrimidin-5-yl | H | H,H,Me(R),H,H,H | | |
| 63 | -pyrimidin-5-yl | H | H,H,Me(S),H,H,H | | |
| 64 | -pyrimidin-5-yl | H | H,H,Me(±),H,H,H | | |
| 65 | -pyrimidin-5-yl | H | Me(R),H,Me(R),H,H,Me(R) | | |
| 66 | -pyrimidin-5-yl | H | Me(R),H,Me(S),H,H,Me(R) | | |
| 67 | -pyrimidin-5-yl | H | Me(S),H,Me(R),H,H,Me(S) | | |
| 68 | -pyrimidin-5-yl | H | Me(S),H,Me(S),H,H,Me(S) | | |
| 69 | -pyrimidin-5-yl | H | Et(R),H,H,H,H,Me(R) | | |
| 70 | -pyrimidin-5-yl | H | Et(S),H,H,H,H,Me(R) | | |
| 71 | -pyrimidin-5-yl | H | Et(R),H,H,H,H,Me(S) | | |
| 72 | -pyrimidin-5-yl | H | Et(S),H,H,H,H,Me(S) | | |
| 73 | -pyrimidin-5-yl | H | Et(R),H,H,H,H,Et(R) | | |
| 74 | -pyrimidin-5-yl | H | Et(S),H,H,H,H,Et(R) | | |
| 75 | -pyrimidin-5-yl | H | Et(R),H,H,H,H,Et(S) | | |
| 76 | -pyrimidin-5-yl | H | Et(S),H,H,H,H,Et(S) | | |
| 77 | -pyrimidin-5-yl | H | Et(R),H,H,H,H,H | | |
| 78 | -pyrimidin-5-yl | H | Et(S),H,H,H,H,H | | |
| 79 | -pyrimidin-5-yl | H | Et(±),H,H,H,H,H | | |
| 80 | -pyrimidin-5-yl | H | H,Et(R),H,H,Et(R),H | | |
| 81 | -pyrimidin-5-yl | H | H,Et(S),H,H,Et(S),H | | |
| 82 | -pyrimidin-5-yl | H | H,Et(±),H,H,Et(±),H | | |
| 83 | -pyrimidin-5-yl | H | H,H,Et(R),H,H,H | | |
| 84 | -pyrimidin-5-yl | H | H,H,Et(S),H,H,H | | |
| 85 | -pyrimidin-5-yl | H | H,H,Et(±),H,H,H | | |
| 86 | -pyrimidin-5-yl | H | Me(R),H,Et(R),H,H,Me(R) | | |
| 87 | -pyrimidin-5-yl | H | Me(R),H,Et(S),H,H,Me(R) | | |
| 88 | -pyrimidin-5-yl | H | Me(S),H,Et(R),H,H,Me(S) | | |
| 89 | -pyrimidin-5-yl | H | Me(S),H,Et(S),H,H,Me(S) | | |
| 90 | -pyrimidin-5-yl | H | Et(R),H,Me(R),H,H,Et(R) | | |
| 91 | -pyrimidin-5-yl | H | Et(R),H,Me(S),H,H,Et(R) | | |
| 92 | -pyrimidin-5-yl | H | Et(S),H,Me(R),H,H,Et(S) | | |
| 93 | -pyrimidin-5-yl | H | Et(S),H,Me(S),H,H,Et(S) | | |
| 94 | -pyrimidin-5-yl | H | Et(R),H,Et(R),H,H,Et(R) | | |
| 95 | -pyrimidin-5-yl | H | Et(R),H,Et(S),H,H,Et(R) | | |
| 96 | -pyrimidin-5-yl | H | Et(S),H,Et(R),H,H,Et(S) | | |
| 97 | -pyrimidin-5-yl | H | Et(S),H,Et(S),H,H,Et(S) | | |
| 98 | -pyrimidin-2-yl | H | Me(S),H,H,H,H,Me(S) | | |
| 99 | -pyrimidin-2-yl | H | Me(R),H,H,H,H,Me(S) | | |
| 100 | -pyrimidin-2-yl | H | Me(±),H,H,H,H,Me(±) | | |
| 101 | -pyrimidin-2-yl | H | H,H,H,H,H,H | | |
| 102 | -pyrimidin-2-yl | H | Me(R),H,H,H,H,H | | |
| 103 | -pyrimidin-2-yl | H | Me(S),H,H,H,H,H | | |
| 104 | -pyrimidin-2-yl | H | Me(±),H,H,H,H,H | | |
| 105 | -pyrimidin-2-yl | H | H,Me(R),H,H,Me(R),H | | |
| 106 | -pyrimidin-2-yl | H | H,Me(S),H,H,Me(S),H | | |

TABLE 2-continued

Symmetrical 3-aryl and 3-heteroaryl substituted bisnaphthalimides of Formula (I): L is diamino linker.

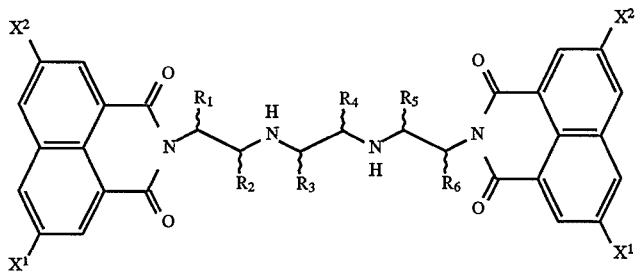

| Ex. | X¹ | X² | $R^1,R^2,R^3,R^4,R^5,R^6$ | Salt | mp °C. |
|---|---|---|---|---|---|
| 107 | -pyrimidin-2-yl | H | H,Me(±),H,H,Me(±),H | | |
| 108 | -pyrimidin-2-yl | H | H,H,Me(R),H,H,H | | |
| 109 | -pyrimidin-2-yl | H | H,H,Me(S),H,H,H | | |
| 110 | -pyrimidin-2-yl | H | H,H,Me(±),H,H,H | | |
| 111 | -pyrimidin-2-yl | H | Me(R),H,Me(R),H,H,Me(R) | | |
| 112 | -pyrimidin-2-yl | H | Me(R),H,Me(S),H,H,Me(R) | | |
| 113 | -pyrimidin-2-yl | H | Me(S),H,Me(R),H,H,Me(S) | | |
| 114 | -pyrimidin-2-yl | H | Me(S),H,Me(S),H,H,Me(S) | | |
| 115 | -pyrimidin-2-yl | H | Et(R),H,H,H,H,Me(R) | | |
| 116 | -pyrimidin-2-yl | H | Et(S),H,H,H,H,Me(R) | | |
| 117 | -pyrimidin-2-yl | H | Et(R),H,H,H,H,Me(S) | | |
| 118 | -pyrimidin-2-yl | H | Et(S),H,H,H,H,Me(S) | | |
| 119 | -pyrimidin-2-yl | H | Et(R),H,H,H,H,Et(R) | | |
| 120 | -pyrimidin-2-yl | H | Et(S),H,H,H,H,Et(R) | | |
| 121 | -pyrimidin-2-yl | H | Et(R),H,H,H,H,Et(S) | | |
| 122 | -pyrimidin-2-yl | H | Et(S),H,H,H,H,Et(S) | | |
| 123 | -pyrimidin-2-yl | H | Et(R),H,H,H,H,H | | |
| 124 | -pyrimidin-2-yl | H | Et(S),H,H,H,H,H | | |
| 125 | -pyrimidin-2-yl | H | Et(±),H,H,H,H,H | | |
| 126 | -pyrimidin-2-yl | H | H,Et(R),H,H,Et(R),H | | |
| 127 | -pyrimidin-2-yl | H | H,Et(S),H,H,Et(S),H | | |
| 128 | -pyrimidin-2-yl | H | H,Et(±),H,H,Et(±),H | | |
| 129 | -pyrimidin-2-yl | H | H,H,Et(R),H,H,H | | |
| 130 | -pyrimidin-2-yl | H | H,H,Et(S),H,H,H | | |
| 131 | -pyrimidin-2-yl | H | H,H,Et(±),H,H,H | | |
| 132 | -pyrimidin-2-yl | H | Me(R),H,Et(R),H,H,Me(R) | | |
| 133 | -pyrimidin-2-yl | H | Me(R),H,Et(S),H,H,Me(R) | | |
| 134 | -pyrimidin-2-yl | H | Me(S),H,Et(R),H,H,Me(S) | | |
| 135 | -pyrimidin-2-yl | H | Me(S),H,Et(S),H,H,Me(S) | | |
| 136 | -pyrimidin-2-yl | H | Et(R),H,Me(R),H,H,Et(R) | | |
| 137 | -pyrimidin-2-yl | H | Et(R),H,Me(S),H,H,Et(R) | | |
| 138 | -pyrimidin-2-yl | H | Et(S),H,Me(R),H,H,Et(S) | | |
| 139 | -pyrimidin-2-yl | H | Et(S),H,Me(S),H,H,Et(S) | | |
| 140 | -pyrimidin-2-yl | H | Et(R),H,Et(R),H,H,Et(R) | | |
| 141 | -pyrimidin-2-yl | H | Et(R),H,Et(S),H,H,Et(R) | | |
| 142 | -pyrimidin-2-yl | H | Et(S),H,Et(R),H,H,Et(S) | | |
| 143 | -pyrimidin-2-yl | H | Et(S),H,Et(S),H,H,Et(S) | | |

TABLE 3

Symmetrical 3-aryl and 3-heteroaryl substituted bisnaphthalimides: L is monoamino linker.

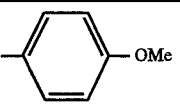

| Ex | X¹ | R⁹ | n | m | salt | mp °C. |
|---|---|---|---|---|---|---|
| 144 | 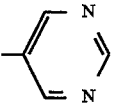 —OMe | H | 2 | 2 | $CH_3SO_3H$ | 133–137 |
| 145 | 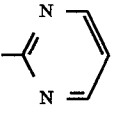 (pyrimidinyl) | H | 1 | 1 | $CH_3SO_3H$ | 254–255 |
| 146 | 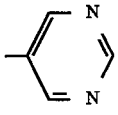 (pyrimidinyl) | H | 1 | 1 | $CH_3SO_3H$ | 300 |
| 147 | 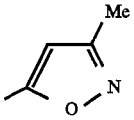 (pyrimidinyl) | Me(R) | 1 | 1 | $CH_3SO_3H$ | 297–299 |
| 148 |  (methylisoxazolyl) | Me(R) | 1 | 1 | $CH_3SO_3H$ | 241–244 |

TABLE 4

Unsymmetrical 3-aryl and 3-heteroaryl substituted bisnaphthalimides

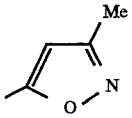

| Ex | X¹ | R¹,R²,R³,R⁴,R⁵,R⁶ | mp °C. |
|---|---|---|---|
| 149 | phenyl | Me(R),H,H,H,H,Me(R) | 187–189 |
| 150 | methylisoxazolyl | Me(R),H,H,H,H,Me(R) | 204–206 |

TABLE 4-continued

Unsymmetrical 3-aryl and 3-heteroaryl substituted bisnaphthalimides

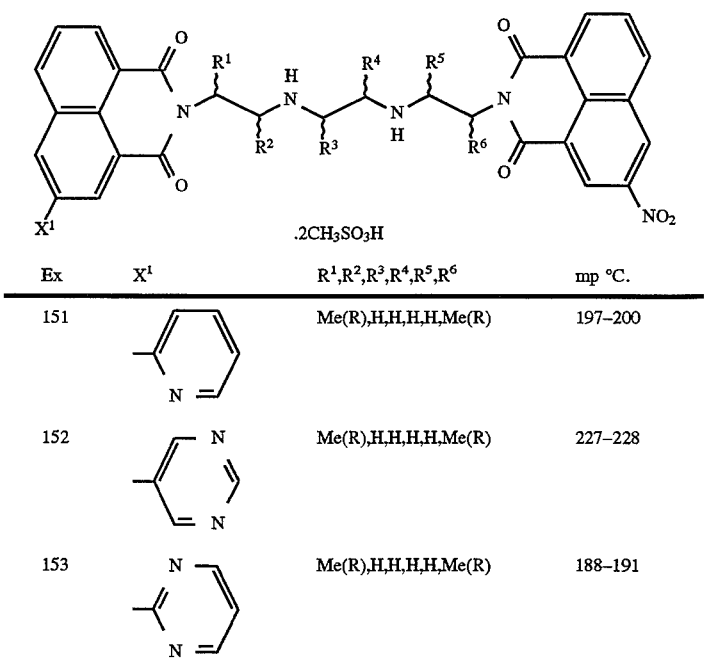

.2CH₃SO₃H

| Ex | X¹ | R¹,R²,R³,R⁴,R⁵,R⁶ | mp °C. |
|---|---|---|---|
| 151 | (2-pyridyl) | Me(R),H,H,H,H,Me(R) | 197–200 |
| 152 | (pyrimidinyl) | Me(R),H,H,H,H,Me(R) | 227–228 |
| 153 | (pyrazinyl) | Me(R),H,H,H,H,Me(R) | 188–191 |

TABLE 5

Unsymmetrical 3-(pyrimidin-5-yl) substituted bisnaphthalimides

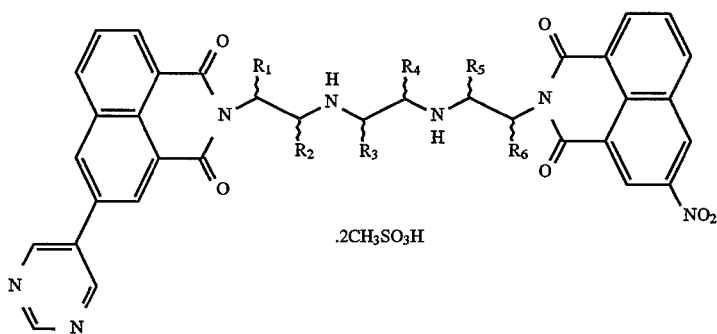

.2CH₃SO₃H $R_1, R_2, R_3, R_4, R_5, R_6$ = see Table below:

| Ex. # | .1 | .2 |
|---|---|---|
| 5.1 | Me(S),H,H,H,H,Me(S) | Et(R),H,H,H,H,H |
| 5.2 | Me(R),H,H,H,H,Me(S) | H,H,H,H,H,Et(R) |
| 5.3 | Me(±),H,H,H,H,Me(±) | Et(S),H,H,H,H,H |
| 5.4 | H,H,H,H,H,H | H,H,H,H,H,Et(S) |
| 5.5 | Me(R),H,H,H,H,H | Et(±),H,H,H,H,H |
| 5.6 | H,H,H,H,H,Me(R) | H,H,H,H,H,Et(±) |
| 5.7 | Me(S),H,H,H,H,H | H,Et(R),H,H,Et(R),H |
| 5.8 | H,H,H,H,H,Me(S) | H,Et(S),H,H,Et(S),H |
| 5.10 | Me(±),H,H,H,H,H | H,Et(±),H,H,Et(±),H |
| 5.11 | H,H,H,H,H,Me(±) | H,H,Et(R),H,H,H |
| 5.12 | H,Me(R),H,H,Me(R),H | H,H,H,Et(R),H,H |
| 5.13 | H,Me(S),H,H,Me(S),H | H,H,Et(S),H,H,H |
| 5.14 | H,Me(±),H,H,Me(±),H | H,H,H,Et(S),H,H |
| 5.15 | H,H,Me(R),H,H,H | H,H,Et(±),H,H,H |
| 5.16 | H,H,H,Me(R),H,H | H,H,H,Et(±),H,H |
| 5.17 | H,H,Me(S),H,H,H | Me(R),H,Et(R),H,H,Me(R) |
| 5.18 | H,H,H,Me(S),H,H | Me(R),H,H,Et(R),H,Me(R) |
| 5.19 | H,H,Me(±),H,H,H | Me(R),H,Et(S),H,H,Me(R) |
| 5.20 | H,H,H,Me(±),H,H | Me(R),H,H,Et(S),H,Me(R) |

TABLE 5-continued

Unsymmetrical 3-(pyrimidin-5-yl) substituted bisnaphthalimides

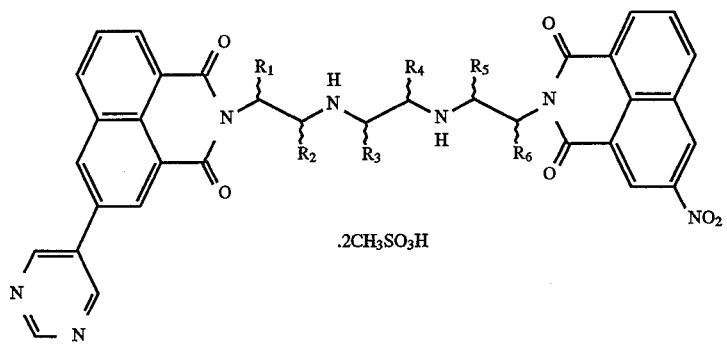

R₁,R₂,R₃,R₄,R₅,R₆ = see Table below:

| Ex. # | .1 | .2 |
|---|---|---|
| 5.21 | Me(R),H,Me(R),H,H,Me(R) | Me(S),H,Et(R),H,H,Me(S) |
| 5.22 | Me(R),H,H,Me(R),H,Me(R) | Me(S),H,H,Et(R),H,Me(S) |
| 5.23 | Me(R),H,Me(S),H,H,Me(R) | Me(S),H,Et(S),H,H,Me(S) |
| 5.23 | Me(R),H,H,Me(S),H,Me(R) | Me(S),H,H,Et(S),H,Me(S) |
| 5.24 | Me(S),H,Me(R),H,H,Me(S) | Et(R),H,Me(R),H,H,Et(R) |
| 5.25 | Me(S),H,Me(R),H,Me(S) | Et(R),H,H,Me(R),H,Et(R) |
| 5.26 | Me(S),H,Me(S),H,H,Me(S) | Et(R),H,Me(S),H,H,Et(R) |
| 5.27 | Me(S),H,H,Me(S),H,Me(S) | Et(R),H,H,Me(S),H,Et(R) |
| 5.28 | Et(R),H,H,H,H,Me(R) | Et(S),H,Me(R),H,H,Et(S) |
| 5.29 | Me(R),H,H,H,H,Et(R) | Et(S),H,H,Me(R),H,Et(S) |
| 5.30 | Et(S),H,H,H,H,Me(R) | Et(S),H,Me(S),H,H,Et(S) |
| 5.31 | Me(R),H,H,H,H,Et(S) | Et(S),H,H,Me(S),H,Et(S) |
| 5.32 | Et(R),H,H,H,H,Me(S) | Et(R),H,Et(R),H,H,Et(R) |
| 5.33 | Me(S),H,H,H,H,Et(R) | Et(R),H,H,Et(R),H,Et(R) |
| 5.34 | Et(S),H,H,H,H,Me(S) | Et(R),H,Et(S),H,H,Et(R) |
| 5.35 | Me(S),H,H,H,H,Et(S) | Et(R),H,H,Et(S),H,Et(R) |
| 5.36 | Et(R),H,H,H,H,Et(R) | Et(S),H,Et(R),H,H,Et(S) |
| 5.37 | Et(S),H,H,H,H,Et(R) | Et(S),H,H,Et(R),H,Et(S) |
| 5.38 | Et(R),H,H,H,H,Et(S) | Et(S),H,Et(S),H,H,Et(S) |
| 5.39 | Et(S),H,H,H,H,Et(S) | Et(S),H,H,Et(S),H,Et(S) |

TABLE 6

Unsymmetrical 3-(pyrimidin-2-yl) substituted bisnaphthalimides

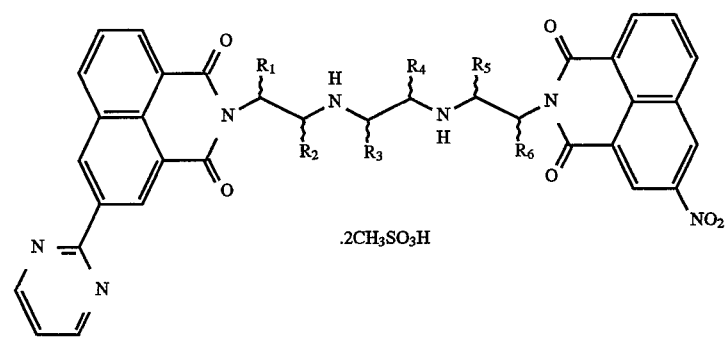

| Ex # | .1 | .2 |
|---|---|---|
| 6.1 | Me(S),H,H,H,H,Me(s) | Et(R),H,H,H,H,H |
| 6.2 | Me(R),H,H,H,H,Me(S) | H,H,H,H,H,Et(R) |
| 6.3 | Me(±),H,H,H,H,Me(±) | Et(S),H,H,H,H,H |
| 6.4 | H,H,H,H,H,H | H,H,H,H,H,Et(S) |
| 6.5 | Me(R),H,H,H,H,H | Et(±),H,H,H,H,H |
| 6.6 | H,H,H,H,H,Me(R) | H,H,H,H,H,Et(±) |
| 6.7 | Me(S),H,H,H,H,H | H,Et(R),H,H,Et(R),H |
| 6.8 | H,H,H,H,H,Me(S) | H,Et(S),H,H,Et(S),H |
| 6.10 | Me(±),H,H,H,H,H | H,Et(±),H,H,Et(±),H |
| 6.11 | H,H,H,H,H,Me(±) | H,H,Et(R),H,H,H |
| 6.12 | H,Me(R),H,H,Me(R),H | H,H,H,Et(R),H,H |

TABLE 6-continued

Unsymmetrical 3-(pyrimidin-2-yl) substituted bisnaphthalimides

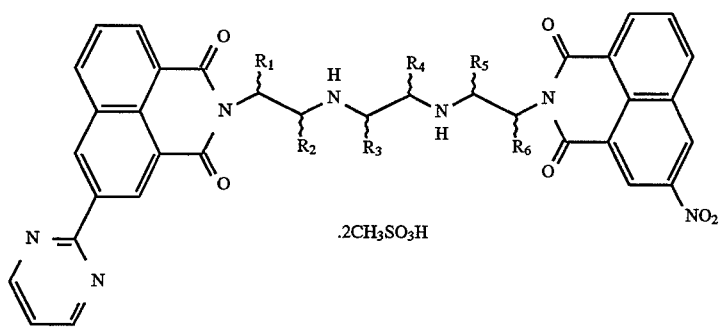

.2CH₃SO₃H

| Ex # | .1 | .2 |
|---|---|---|
| 6.13 | H,Me(S),H,H,Me(S),H | H,H,Et(S),H,H,H |
| 6.14 | H,Me(±),H,H,Me(±),H | H,H,H,Et(S),H,H |
| 6.15 | H,H,Me(R),H,H,H | H,H,Et(±),H,H,H |
| 6.16 | H,H,H,Me(R),H,H | H,H,H,Et(±),H,H |
| 6.17 | H,H,Me(S),H,H,H | Me(R),H,Et(R),H,H,Me(R) |
| 6.18 | H,H,H,Me(S),H,H | Me(R),H,H,Et(R),H,Me(R) |
| 6.19 | H,H,Me(±),H,H,H | Me(R),H,Et(S),H,H,Me(R) |
| 6.20 | H,H,H,Me(±),H,H | Me(R),H,H,Et(S),H,Me(R) |
| 6.21 | Me(R),H,Me(R),H,H,Me(R) | Me(S),H,Et(R),H,H,Me(S) |
| 6.22 | Me(R),H,H,Me(R),H,Me(R) | Me(S),H,H,Et(R),H,Me(S) |
| 6.23 | Me(R),H,Me(S),H,H,Me(R) | Me(S),H,Et(S),H,H,Me(S) |
| 6.23 | Me(R),H,H,Me(S),H,Me(R) | Me(S),H,H,Et(S),H,Me(S) |
| 6.24 | Me(S),H,Me(R),H,H,Me(S) | Et(R),H,Me(R),H,H,Et(R) |
| 6.25 | Me(S),H,H,Me(R),H,Me(S) | Et(R),H,H,Me(R),H,Et(R) |
| 6.26 | Me(S),H,Me(S),H,H,Me(S) | Et(R),H,Me(S),H,H,Et(R) |
| 6.27 | Me(S),H,H,Me(S),H,Me(S) | Et(R),H,H,Me(S),H,Et(R) |
| 6.28 | Et(R),H,H,H,H,Me(R) | Et(S),H,Me(R),H,H,Et(S) |
| 6.29 | Me(R),H,H,H,H,Et(R) | Et(S),H,H,Me(R),H,Et(S) |
| 6.30 | Et(S),H,H,H,H,Me(R) | Et(S),H,Me(S),H,H,Et(S) |
| 6.31 | Me(R),H,H,H,H,Et(S) | Et(S),H,H,Me(S),H,Et(S) |
| 6.32 | Et(R),H,H,H,H,Me(S) | Et(R),H,Et(R),H,H,Et(R) |
| 6.33 | Me(S),H,H,H,H,Et(R) | Et(R),H,H,Et(R),H,Et(R) |
| 6.34 | Et(S),H,H,H,H,Me(S) | Et(R),H,Et(S),H,H,Et(R) |
| 6.35 | Me(S),H,H,H,H,Et(S) | Et(R),H,H,Et(S),H,Et(R) |
| 6.36 | Et(R),H,H,H,H,Et(R) | Et(S),H,Et(R),H,H,Et(S) |
| 6.37 | Et(S),H,H,H,H,Et(R) | Et(S),H,H,Et(R),H,Et(S) |
| 6.38 | Et(R),H,H,H,H,Et(S) | Et(S),H,Et(S),H,H,Et(S) |
| 6.39 | Et(S),H,H,H,H,Et(S) | Et(S),H,H,Et(S),H,Et(S) |

TABLE 7

Unsymmetrical 3-(pyridin-2-yl) substituted bisnaphthalimides

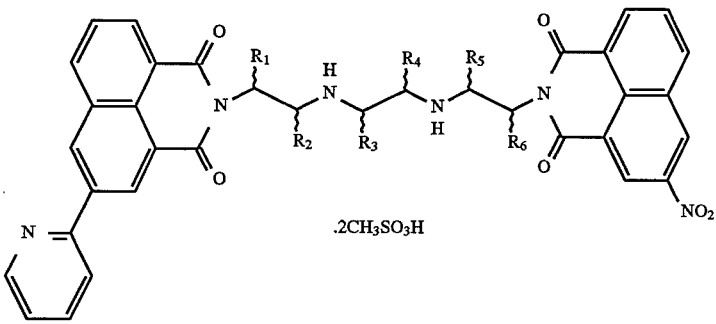

.2CH₃SO₃H

| Ex # | .1 | .2 |
|---|---|---|
| 7.1 | Me(S),H,H,H,H,Me(S) | Et(R),H,H,H,H,H |
| 7.2 | Me(R),H,H,H,H,Me(S) | H,H,H,H,H,Et(R) |
| 7.3 | Me(±),H,H,H,H,Me(±) | Et(S),H,H,H,H,H |
| 7.4 | H,H,H,H,H,H | H,H,H,H,H,Et(S) |
| 7.5 | Me(R),H,H,H,H,H | Et(±),H,H,H,H,H |

TABLE 7-continued

Unsymmetrical 3-(pyridin-2-yl) substituted bisnaphthalimides

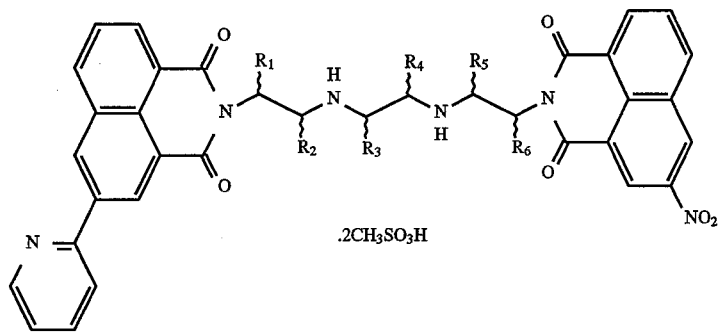

.2CH₃SO₃H

| Ex # | .1 | .2 |
|---|---|---|
| 7.6 | H,H,H,H,H,Me(R) | H,H,H,H,H,Et(±) |
| 7.7 | Me(S),H,H,H,H,H | H,Et(R),H,H,Et(R),H |
| 7.8 | H,H,H,H,H,Me(S) | H,Et(S),H,H,Et(S),H |
| 6.10 | Me(±),H,H,H,H,H | H,Et(±),H,H,Et(±),H |
| 7.11 | H,H,H,H,H,Me(±) | H,H,Et(R),H,H,H |
| 7.12 | H,Me(R),H,H,Me(R),H | H,H,H,Et(R),H,H |
| 7.13 | H,Me(S),H,H,Me(S),H | H,H,Et(S),H,H,H |
| 7.14 | H,Me(±),H,H,Me(±),H | H,H,H,Et(S),H,H |
| 7.15 | H,H,Me(R),H,H,H | H,H,Et(±),H,H,H |
| 7.16 | H,H,H,Me(R),H,H | H,H,H,Et(±),H,H |
| 7.17 | H,H,Me(S),H,H,H | Me(R),H,Et(R),H,H,Me(R) |
| 7.18 | H,H,H,Me(S),H,H | Me(R),H,H,Et(R),H,Me(R) |
| 7.19 | H,H,Me(±),H,H,H | Me(R),H,Et(S),H,H,Me(R) |
| 7.20 | H,H,H,Me(±),H,H | Me(R),H,H,Et(S),H,Me(R) |
| 7.21 | Me(R),H,Me(R),H,H,Me(R) | Me(S),H,Et(R),H,H,Me(S) |
| 7.22 | Me(R),H,H,Me(R),H,Me(R) | Me(S),H,H,Et(R),H,Me(S) |
| 7.23 | Me(R),H,Me(S),H,H,Me(R) | Me(S),H,Et(S),H,H,Me(S) |
| 7.23 | Me(R),H,H,Me(S),H,Me(R) | Me(S),H,H,Et(S),H,Me(S) |
| 7.24 | Me(S),H,Me(R),H,H,Me(S) | Et(R),H,Me(R),H,H,Et(R) |
| 7.25 | Me(S),H,H,Me(R),H,Me(S) | Et(R),H,H,Me(R),H,Et(R) |
| 7.26 | Me(S),H,Me(S),H,H,Me(S) | Et(R),H,Me(S),H,H,Et(R) |
| 7.27 | Me(S),H,H,Me(S),H,Me(S) | Et(R),H,H,Me(S),H,Et(R) |
| 7.28 | Et(R),H,H,H,H,Me(R) | Et(S),H,Me(R),H,H,Et(S) |
| 7.29 | Me(R),H,H,H,H,Et(R) | Et(S),H,H,Me(R),H,Et(S) |
| 7.30 | Et(S),H,H,H,H,Me(R) | Et(S),H,Me(S),H,H,Et(S) |
| 7.31 | Me(R),H,H,H,H,Et(S) | Et(S),H,H,Me(S),H,Et(S) |
| 7.32 | Et(R),H,H,H,H,Me(S) | Et(R),H,Et(R),H,H,Et(R) |
| 7.33 | Me(S),H,H,H,H,Et(R) | Et(R),H,H,Et(R),H,Et(R) |
| 7.34 | Et(S),H,H,H,H,Me(S) | Et(R),H,Et(S),H,H,Et(R) |
| 7.35 | Me(S),H,H,H,H,Et(S) | Et(R),H,H,Et(S),H,Et(R) |
| 7.36 | Et(R),H,H,H,H,Et(R) | Et(S),H,Et(R),H,H,Et(S) |
| 7.37 | Et(S),H,H,H,H,Et(R) | Et(S),H,H,Et(R),H,Et(S) |
| 7.38 | Et(R),H,H,H,H,Et(S) | Et(S),H,Et(S),H,H,Et(S) |
| 7.39 | Et(S),H,H,H,H,Et(S) | Et(S),H,H,Et(S),H,Et(S) |

TABLE 8

Unsymmetrical 3-(3-methylisoxazol-5-yl) substituted bisnaphthalimides

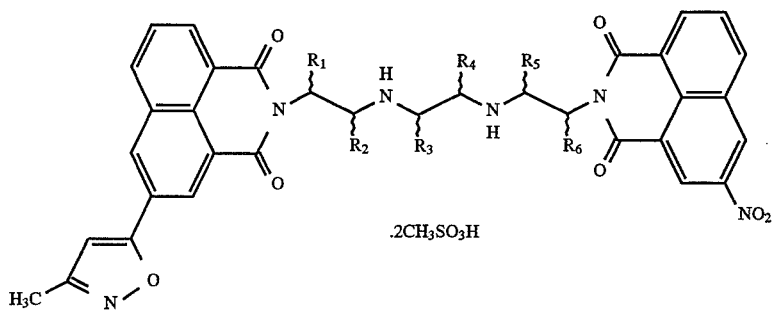

.2CH₃SO₃H

| Ex # | .1 | .2 |
|---|---|---|
| 8.1 | Me(S),H,H,H,H,Me(S) | Et(R),H,H,H,H,H |
| 8.2 | Me(R),H,H,H,H,Me(S) | H,H,H,H,H,Et(R) |
| 8.3 | Me(±),H,H,H,H,Me(±) | Et(S),H,H,H,H,H |
| 8.4 | H,H,H,H,H,H | H,H,H,H,H,Et(S) |
| 8.5 | Me(R),H,H,H,H,H | Et(±),H,H,H,H,H |
| 8.6 | H,H,H,H,H,Me(R) | H,H,H,H,H,Et(±) |
| 8.7 | Me(S),H,H,H,H,H | H,Et(R),H,H,Et(R),H |
| 8.8 | H,H,H,H,H,Me(S) | H,Et(S),H,H,Et(S),H |
| 8.10 | Me(±),H,H,H,H,H | H,Et(±),H,H,Et(±),H |
| 8.11 | H,H,H,H,H,Me(±) | H,H,Et(R),H,H,H |
| 8.12 | H,Me(R),H,H,Me(R),H | H,H,H,Et(R),H,H |
| 8.13 | H,Me(S),H,H,Me(S),H | H,H,Et(S),H,H,H |
| 8.14 | H,Me(±),H,H,Me(±),H | H,H,H,Et(S),H,H |
| 8.15 | H,H,Me(R),H,H,H | H,H,Et(±),H,H,H |
| 8.16 | H,H,H,Me(R),H,H | H,H,H,Et(±),H,H |
| 8.17 | H,H,Me(S),H,H,H | Me(R),H,Et(R),H,H,Me(R) |
| 8.18 | H,H,H,Me(S),H,H | Me(R),H,H,Et(R),H,Me(R) |
| 8.19 | H,H,Me(±),H,H,H | Me(R),H,Et(S),H,H,Me(R) |
| 8.20 | H,H,H,Me(±),H,H | Me(R),H,H,Et(S),H,Me(R) |
| 8.21 | Me(R),H,Me(R),H,H,Me(R) | Me(S),H,Et(R),H,H,Me(S) |
| 8.22 | Me(R),H,H,Me(R),H,Me(R) | Me(S),H,H,Et(R),H,Me(S) |
| 8.23 | Me(R),H,Me(S),H,H,Me(R) | Me(S),H,Et(S),H,H,Me(S) |
| 8.23 | Me(R),H,H,Me(S),H,Me(R) | Me(S),H,H,Et(S),H,Me(S) |
| 8.24 | Me(S),H,Me(R),H,H,Me(S) | Et(R),H,Me(R),H,H,Et(R) |
| 8.25 | Me(S),H,H,Me(R),H,Me(S) | Et(R),H,H,Me(R),H,Et(R) |
| 8.26 | Me(S),H,Me(S),H,H,Me(S) | Et(R),H,Me(S),H,H,Et(R) |
| 8.27 | Me(S),H,H,Me(S),H,Me(S) | Et(R),H,H,Me(S),H,Et(R) |
| 8.28 | Et(R),H,H,H,H,Me(R) | Et(S),H,Me(R),H,H,Et(S) |
| 8.29 | Me(R),H,H,H,H,Et(R) | Et(S),H,H,Me(R),H,Et(S) |
| 8.30 | Et(S),H,H,H,H,Me(R) | Et(S),H,Me(S),H,H,Et(S) |
| 8.31 | Me(R),H,H,H,H,Et(S) | Et(S),H,H,Me(S),H,Et(S) |
| 8.32 | Et(R),H,H,H,H,Me(S) | Et(R),H,Et(R),H,H,Et(R) |
| 8.33 | Me(S),H,H,H,H,Et(R) | Et(R),H,H,Et(R),H,Et(R) |
| 8.34 | Et(S),H,H,H,H,Me(S) | Et(R),H,Et(S),H,H,Et(R) |
| 8.35 | Me(S),H,H,H,H,Et(S) | Et(R),H,H,Et(S),H,Et(R) |
| 8.36 | Et(R),H,H,H,H,Et(R) | Et(S),H,Et(R),H,H,Et(S) |
| 8.37 | Et(S),H,H,H,H,Et(R) | Et(S),H,H,Et(R),H,Et(S) |
| 8.38 | Et(R),H,H,H,H,Et(S) | Et(S),H,Et(S),H,H,Et(S) |
| 8.39 | Et(S),H,H,H,H,Et(S) | Et(S),H,H,Et(S),H,Et(S) |

Utility

In vitro Growth Inhibitory Activity

L1210 cells were maintained in RPMI-1640 a medium supplemented with 10% heat inactivated fetal bovine serum and 50 mL mercaptoethanol/liter medium (RPMI-L).

Exponentially growing murine leukemia L1210 cells (1×10³ cells) in 0.1 mL medium were seeded on day 0 in a 96-well microtiter plate. On day. 1, 0.1 mL aliquot of medium containing graded concentrations of test analogs was added to the initial volume. After incubation at 37 ° C. in a humidified incubator for 3 days the plates were centrifuged briefly and 100 mL of the growth medium was removed.

Exponentially growing human colon Clone A cells (8×10²) in 0.1 mL medium were seeded on day 0 in a 96-well microtiter plate. On day 1, 0.1 mL of medium containing graded concentrations of test analogs was added to the initial volume. After incubation at 37° C. in a humidified incubator for 6 days, the plates were centrifuged briefly and 0.1 mL of the growth medium was removed.

The cell cultures (above) were then incubated with 50 mL of 3-(4,5-dimethylthiazol-2-yl)-2,5-diphenyltetrazolium bromide (MTT; 1 mg/ml in Dulbecco's phosphate buffer saline) for 4 hours at 37° C. The resulting purple formazan precipitate was solubilized with 200 mL of 0.04N HCl in isopropyl alcohol. Absorbance was read in a Titertek Multiskan MCC scanning well spectrophotometer (Flow Laboratories) at a test wavelength of 570 nm and a reference wavelength of 630 nm.

The $ID_{50}$ values were determined by a computer program that fits all of the data (8 determinations per concentration and 12 concentrations per test analog) to the following equation:

$$Y=((Am-Ao)/(1+(X/ID_{50})n))+Ao$$

where: Am=absorbance of the control cells; Ao=absorbance of the cells in the presence of highest drug concentration; Y=observed absorbance; X=drug concentration; $ID_{50}$ =dose of drug that inhibits the growth of cells to one half that of the control cells.

Results of the in vitro L1210 leukemia and Clone A colon carcinoma growth inhibition testing show that the compounds of this invention that were tested in these assays have $ID_{50}$ value of less than 0.9 µg/mL and less than 2.2 µg/mL, respectively.

In Vivo Tumor Models

The methods used in the testing of compounds in the in vivo human tumor xenograft models are described below.

In Vivo Human Tumor Xenograft Models

The MX-1 human mammary carcinoma and the LX-1 human lung carcinoma were originally obtained from a surgically removed primary breast tumor and lung carcinoma, respectively. The human tumor lines were maintained by serial passage in athymic nude mice. The MX-1 human mammary carcinoma is an established tumor used by the NCI. The MX-1 and LX-1 tumor models have been well characterized.

The mice used in these experiments were outbred Swiss mice or BALB/c mice bearing the nude (nu/nu) gene. On day 0 male and female mice weighing 22–30 g are inoculated with 0.2 mL of a 25% tumor mince. This mince is prepared by mincing fresh tumor tissue, grown subcutaneously in passage mice, in sterile physiological saline. Palpable tumors weighing approximately 50 mg appear in the mice within 7–10 days after inoculation. The mice are pair matched by tumor weight and sex into groups of ten each and the test compounds and vehicle control are administered intravenously (iv.) once daily for nine consecutive days. A >20% decrease in body weight on day 5 following compound administration is considered an indication of toxicity. Tumor measurements and body weights are recorded once a week. Fifteen to 18 days after the initial injection the mice are weighed, sacrificed and the tumors excised and weighed.

The efficacy of the test compounds is determined by the extent of tumor growth inhibition in treated versus vehicle-treated control mice. Initial tumor weights (mg) are calculated from the tumor dimensions (mm) measured from caliper measurements, using the formula for a prolate ellipsoid (mg of tumor weight=(length×width$^2$)/2). Net tumor weights are calculated for each of the treated groups and the vehicle-treated control group by subtracting the initial tumor weight from the final tumor weight on day 15. Results are expressed as a percentage decrease relative to the mean tumor weight for the control vehicle-treated group.

$$\% \text{ Tumor Growth Inhibition} = \left[ 1 - \frac{\text{mean tumor weight of treated}}{\text{mean tumor weight of control}} \right] \times 100$$

Activity Criteria

The criteria of the National Cancer Institute (NCI) for activity in the in vivo cancer models were used. Actual tumor regressions (IR=incomplete regression; FR=full regression; NT=not tested) indicate excellent to outstanding activity. Tumor growth inhibition of ≧90% in the LX-1 assay is considered good to excellent and inhibition of 58–89% is considered moderate. Compounds demonstrating <58% growth inhibition are considered inactive.

Some of compounds of this invention which were tested exhibited activity in the MX-1 human breast tumor model. In addition, compounds of this invention which were tested in the LX-1 human lung tumor model exhibited activity.

The demonstrated effectiveness of the compounds of the present invention in the human breast and lung tumor xenograft models indicate that the compounds of the present invention are useful for the treatment of solid tumors in man, and, in particular, tumors of the breast and lung. This conclusion is further supported by published analyses correlating pre-clinical test results with clinical efficacy of anti-cancer agents. For example, see: Goldin and Venditti (1980) Recent Results Cancer Research 76: 176–191; Goldin et al. (1981) Eur. J. Cancer 17: 129–142; Mattern et al. (1988) Cancer and Metastasis Review 7: 263–284; Jackson et al. (1990) Cancer Investigations 8: 39–47. Based on these published analyses, the exceptional high level of antitumor activity exhibited by the presently claimed compounds provide strong evidence that the compounds claimed in present invention have therapeutic utility in the treatment of cancer in man.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 1 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules: Capsules are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98 milligrams of lactose. Appropriate coatings may be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure, it should be understood that the specified materials and conditions are important in practicing the invention but that unspecified materials and conditions are not excluded so long as they do not prevent the benefits of the invention from being realized.

What is claimed is:

1. A compound of the formula (I)

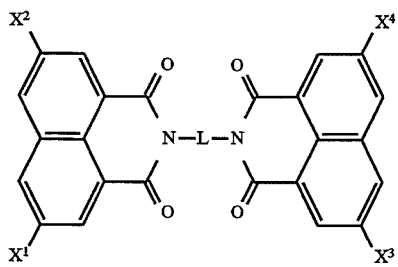

and enantiomeric or diastereomeric forms thereof, or mixtures of enantiomeric or diastereomeric forms thereof, or pharmaceutically acceptable salts thereof, wherein:

L is:

a)

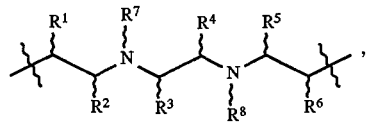

or b)

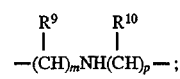

$R^1$, $R^2$, $R^3$, $R^4$, $R^5$, $R^6$, $R^9$ and $R^{10}$ are independently selected from the group: H, $CH_3$ or $C_2H_5$;

$R^7$ and $R^8$ are independently selected from the group consisting of H or $CH_3$;

$X^1$, $X^2$, $X^3$, $X^4$ are independently selected from the group consisting of: H, $NO_2$, aryl, or heteroaryl, where aryl or heteroaryl may be optionally substituted with 1-2 groups independently selected from:
$C_1$-$C_2$ alkyl, $C_1$-$C_2$ alkoxy, CN, $NO_2$, halogen, aminocarbonyl, mono($C_1$-$C_2$ alkyl)aminocarbonyl, di($C_1$-$C_2$ alkyl)aminocarbonyl, amino, $C_1$-$C_2$ alkoxycarbonyl, hydroxycarbonyl, mono($C_1$-$C_2$ alkyl)amino, di($C_1$-$C_2$ alkyl)amino, $C_1$-$C_2$ alkylsulfonyl, mono($C_1$-$C_2$ alkyl)aminosulfonyl, and di($C_1$-$C_2$ alkyl)aminosulfonyl;

aryl is a phenyl group;

heteroaryl is an optionally substituted pyrimidinyl, m is 1, 2 or 3;

p is 1, 2, 3 or 4;

provided that:

1) at least one of $X^1$ and $X^2$ is pyrimidinyl.

2. A compound of claim 1, wherein:

$R^1$, $R^2$, $R^3$, $R^4$, $R^5$, $R^6$ and $R^9$ are independently selected from the group: H or $CH_3$;

$R^7$ and $R^8$ are independently selected from the group: H or $CH_3$;

$R^{10}$ is H;

$X^1$ and $X^2$ are as follows:
1) $X^1$ is optionally substituted aryl or pyrimidinyl when $X^2$ is $NO_2$; or
2) $X^1$ is optionally substituted aryl or pyrimidinyl when $X^2$ is H;

$X^3$ and $X^4$ are as follows:
1) $X^3$ is optionally substituted aryl or pyrimidinyl when $X^4$ is $NO_2$;
2) $X^3$ is optionally substituted aryl or pyrimidinyl when $X^4$ is H; or
3) $X^3$ is H when $X^4$ is $NO_2$;

$X^1$ and $X^3$, when aryl or pyrimidinyl, are independently optionally substituted with 1–2 groups selected from:
$C_1$-$C_2$ alkyl, $C_1$-$C_2$ alkoxy, CN, $NO_2$, halogen, aminocarbonyl, mono($C_1$-$C_2$ alkyl)aminocarbonyl, di($C_1$-$C_2$ alkyl)aminocarbonyl, amino, $C_1$-$C_2$ alkoxycarbonyl, hydroxycarbonyl, mono($C_1$-$C_2$ alkyl)amino, di($C_1$-$C_2$ alkyl)amino; pyrimidinyl, m is 2 or 3;

p is 3 or 4;

and pharmaceutically acceptable salts thereof, and enantiomeric or diastereomeric forms thereof.

3. A compound of claim 2, wherein:

L is

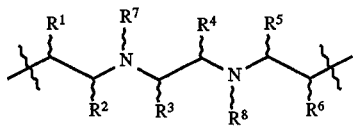

$R^1$, $R^6$ are $CH_3$;

$R^2$, $R^3$, $R^4$, $R^5$, $R^7$, and $R^8$ are H;

$X^1$ is optionally substituted pyrimidinyl;

$X^2$ is H;

$X^3$ and $X^4$ are as follows:
1) $X^3$ is optionally substituted heteroaryl when $X^4$ is H; or
2) $X^3$ is H when $X^4$ is $NO_2$;

$X^1$ and $X^3$, when heteroaryl, are independently optionally substituted with 1-2 groups selected from:
$CH_3$, $NO_2$, hydroxycarbonyl, mono($C_1$-$C_2$ alkyl) amino, or di($C_1$-$C_2$ alkyl)amino;

heteroaryl is an optionally substituted 5- or 6-membered heteroaromatic ring independently selected at each occurrence from the group consisting of;

and pharmaceutically acceptable salts thereof, and enantiomeric or diastereomeric forms thereof.

4. A compound of claim 3, wherein:

$X^1$ and $X^3$, when heteroaryl, are independently substituted with $CH_3$;

heteroaryl is an optionally substituted 5- or 6-membered heteroaromatic ring independently selected at each occurrence from the group consisting of: pyrimidinyl;

and pharmaceutically acceptable salts thereof, and enantiomeric or diastereomeric forms thereof.

5. A compound of claim 4 selected from the group consisting of:

[R-(R*,R*)]-2,2'-[1,2-ethanediylbis[imino(1-methyl-2,1-ethanediyl)]]bis[5-(5-pyrimidinyl)-1H-benz(de) isoquinoline-1,3(2H)-dione]methanesulfonate (1:2),

[R-(R*,R*)]-2-[1-methyl-2-[[2-[[2-(5-nitro-1,3-dioxo-1H-benz(de)isoquinolin-2(3H)-yl)propyl]amino]ethyl] amino]ethyl]-5-(5-pyrimidinyl)-1H-benz(de)-isoquinoline-1,3(2H)-dione methanesulfonate (1:2),

[R-(R*,R*)]-2-[1-methyl-2-[[2-[[2-(5-nitro-1,3-dioxo-1H-benz(de)isoquinolin-2(3H)-yl)propyl]amino]ethyl] amino]ethyl]-5-(2-pyrimidinyl)-1H-benz(de)-isoquinoline-1,3(2H)-dione methanesulfonate (1:2),

[S-(R*,R*)]-2,2'-[1,2-ethanediylbis[imino(1-methyl-2,1-ethanediyl)]]bis[5-(5-pyrimidinyl)-1H-benz(de) isoquinoline-1,3(2H)-dione]methanesulfonate (1:2),

[S-(R*,R*)]-2-[1-methyl-2-[[2-[[2-(5-nitro-1,3-dioxo-1H-benz(de)isoquinolin-2(3H)-yl)propyl]amino]ethyl] amino]ethyl]-5-(5-pyrimidinyl)- 1H-benz(de)-isoquinoline-1,3(2H)-dione methanesulfonate (1:2),

[S-(R*,R*)]-2-[1-methyl-2-[[2-[[2-(5-nitro-1,3-dioxo-1H-benz(de)isoquinolin-2(3H)-yl)propyl]amino]ethyl] amino]ethyl]-5-(2-pyrimidinyl)-1H-benz(de)-isoquinoline-1,3(2H)-dione methanesulfonate (1:2), (R*,S*)-2,2'-[1,2-ethanediylbis[imino(1-methyl-2,1-ethanediyl)]]bis[5-(5-pyrimidinyl)-1H-benz(de) isoquinoline-1,3(2H)-dione]methanesulfonate (1:2), (R*,S*)-2-[1-methyl-2-[[2-[[2-(5-nitro-1,3-dioxo-1H-benz(de)isoquinolin-2(3H)-yl)propyl]amino]ethyl] amino]ethyl]-5-(5-pyrimidinyl)-1H-benz(de)-isoquinoline-1,3(2H)-dione methanesulfonate (1:2), (R*,S*)-2-[1-methyl-2-[[2-[[2-(5-nitro-1,3-dioxo-1H-benz(de)isoquinolin-2(3H)-yl)propyl]amino]ethyl] amino]ethyl]-5-(2-pyrimidinyl)- 1H-benz(de)-isoquinoline-1,3(2H)-dione methanesulfonate (1:2);

and pharmaceutically acceptable salts thereof.

6. A pharmaceutical composition comprising a pharmaceutically suitable carrier and a therapeutically effective amount of a compound of claim 1.

7. A pharmaceutical composition comprising a pharmaceutically suitable carrier and a therapeutically effective amount of a compound of claim 2.

8. A pharmaceutical composition comprising a pharmaceutically suitable carrier and a therapeutically effective amount of a compound of claim 3.

9. A pharmaceutical composition comprising a pharmaceutically suitable carrier and a therapeutically effective amount of a compound of claim 4.

10. A pharmaceutical composition comprising a pharmaceutically suitable carrier and a therapeutically effective amount of a compound of claim 5.

11. A method of treating a solid tumor carcinoma in a mammal comprising administering to a mammal in need of such treatment a therapeutically effective amount of a compound of claim 1.

12. A method of treating a solid tumor carcinoma in a mammal comprising administering to a mammal in need of such treatment a therapeutically effective amount of a compound of claim 2.

13. A method of treating a solid tumor carcinoma in a mammal comprising administering to a mammal in need of such treatment a therapeutically effective amount of a compound of claim 3.

14. A method of treating a solid tumor carcinoma in a mammal comprising administering to a mammal in need of such treatment a therapeutically effective amount of a compound of claim 4.

15. A method of treating a solid tumor carcinoma in a mammal comprising administering to a mammal in need of such treatment a therapeutically effective amount of a compound of claim 5.

16. A compound of claim 1, wherein:

L is

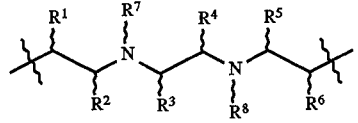

$R^1$, $R^2$, $R^3$, $R^4$, $R^5$, $R^6$, are independently selected from the group: H, or $CH_3$;

$R^7$ and $R^8$ are independently selected from the group consisting of H or $CH_3$;

$X^1$ and $X^3$, are independently pyrimidinyl;

and pharmaceutically acceptable salts thereof, and enantiomeric or diastereomeric forms thereof.

* * * * *